(12) United States Patent
Marumoto et al.

(10) Patent No.: US 10,478,098 B2
(45) Date of Patent: Nov. 19, 2019

(54) INFORMATION PROCESSING SYSTEM

(71) Applicant: FUJI XEROX CO., LTD., Tokyo (JP)

(72) Inventors: Mizuha Marumoto, Tokyo (JP);
Yukari Sai, Tokyo (JP); Yuka Nomura, Kanagawa (JP); Yukiko Miyakoshi, Kanagawa (JP); Kengo Tokuchi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 16/120,567

(22) Filed: Sep. 4, 2018

(65) Prior Publication Data
US 2019/0239777 A1 Aug. 8, 2019

(30) Foreign Application Priority Data

Feb. 2, 2018 (JP) .................................. 2018-017272

(51) Int. Cl.
*A61B 5/11* (2006.01)
*G08B 5/22* (2006.01)
*A47G 9/02* (2006.01)
*A47C 31/11* (2006.01)
*A61B 5/024* (2006.01)

(52) U.S. Cl.
CPC ............. *A61B 5/1116* (2013.01); *A47C 31/11* (2013.01); *A47G 9/0223* (2013.01); *G08B 5/22* (2013.01); *A61B 5/024* (2013.01); *A61B 2562/0247* (2013.01); *A61B 2562/0252* (2013.01); *A61B 2562/0271* (2013.01)

(58) Field of Classification Search
CPC ....... A61B 5/1116; A61B 5/6891; A61B 5/00;
A61B 5/002; A61B 5/0008; A61B 5/0205; A61B 5/01; A61B 5/11; A61B 5/103; A47C 31/11; A47G 9/0223; G08B 5/22; G08B 21/00
USPC ......... 340/539.11, 573.7, 666, 667; 177/144; 181/273; 600/300, 301
See application file for complete search history.

(56) References Cited

U.S. PATENT DOCUMENTS

| | | | | |
|---|---|---|---|---|
| 6,957,591 | B2 * | 10/2005 | Takafuji | G01G 19/4142 73/862.391 |
| 8,477,039 | B2 * | 7/2013 | Gleckler | A61B 5/103 181/273 |
| 9,492,120 | B2 * | 11/2016 | Horseman | G06F 19/3418 |
| 9,795,322 | B1 * | 10/2017 | Karunaratne | A47C 7/72 |
| 2017/0215736 | A1 | 8/2017 | Hu | |

FOREIGN PATENT DOCUMENTS

| | | |
|---|---|---|
| JP | 2002-336095 A | 11/2002 |
| JP | 2003-102801 A | 4/2003 |
| JP | 2008-264188 A | 11/2008 |
| JP | 2017-23475 A | 2/2017 |

* cited by examiner

*Primary Examiner* — Hung T Nguyen
(74) *Attorney, Agent, or Firm* — Oliff PLC

(57) ABSTRACT

An information processing system includes: a sheet that is usable in a use mode which is any one of an underlay mode and a cover mode; an accumulation unit that accumulates relevant information related to when the sheet is used in association with the use mode of the sheet when being used; and a presentation unit that presents a result of analysis of the information accumulated in the accumulation unit, in consideration of the use mode.

20 Claims, 12 Drawing Sheets

FIG. 6

| user-A | | | | | | |
|---|---|---|---|---|---|---|
| DATE/TIME | USE MODE | POSITION | DETECTED LOAD | POSTURE | HEART RATE |
| 2018/02/20/09:15 | UNDERLAY | FIRST OFFICE | (8.5, 8.4, ..., 1.2) | GOOD | 65 |
| 2018/02/20/09:50 | NON-USE | FIRST OFFICE | — | — | — |
| 2018/02/20/09:54 | UNDERLAY | FIRST OFFICE | (8.6, 8.2, ..., 1.3) | GOOD | 70 |
| 2018/02/20/10:51 | UNDERLAY | FIRST OFFICE | (5.2, 8.0, ..., 3.5) | BAD | 68 |
| 2018/02/20/12:02 | UNKNOWN | FIRST OFFICE | (1.1, 2.1, ..., 1.5) | — | 3 |
| 2018/02/20/12:10 | COVER | FIRST DINING-ROOM | — | — | — |
| 2018/02/20/12:50 | UNKNOWN | FIRST DINING-ROOM | (1.1, 2.1, ..., 1.5) | — | 0 |
| 2018/02/20/12:52 | NON-USE | FIRST OFFICE | — | — | — |
| 2018/02/20/13:05 | COVER | SECOND MEETING ROOM | — | — | — |

FIG. 7

| USER ID | user-A |
|---|---|
| SHEET DEVICE ID | 123456789 |
| DIRT COEFFICIENT (UNDERLAY) | 1.0 per hour |
| DIRT COEFFICIENT (COVER) | 0.5 per hour |
| CUMULATIVE DIRT VALUE | 28/100 |

FIG. 8

| user-A | | | | | |
|---|---|---|---|---|---|
| DATE | TIME SEATED | UNDERLAY TIME | COVER TIME | GOOD POSTURE TIME | BAD POSTURE TIME |
| 02/19 | 4.5 | 4.5 | 0 | 3.8 | 0.7 |
| 02/20 | 6.1 | 4.5 | 1.6 | 4.0 | 0.5 |
| ... | | ... | ... | | ... |

INFORMATION PROCESSING SYSTEM

CROSS-REFERENCE TO RELATED APPLICATIONS

This application is based on and claims priority under 35 USC 119 from Japanese Patent Application No. 2018-017272 filed on Feb. 2, 2018.

BACKGROUND

Technical Field

The present invention relates to an information processing system.

SUMMARY

According to an aspect of the invention, there is provided an information processing system including: a sheet that is usable in a use mode which is any one of an underlay mode and a cover mode; an accumulation unit that accumulates relevant information related to when the sheet is used in association with the use mode of the sheet when being used; and a presentation unit that presents a result of analysis of the information accumulated in the accumulation unit, in consideration of the use mode.

BRIEF DESCRIPTION OF THE DRAWINGS

Exemplary embodiment of the present invention will be described in detail based on the following figures, wherein:

FIG. 6 is a table illustrating an example of detection data, recorded on a database, of a sensor group of the sheet-shaped device;

FIG. 7 is a table illustrating the contents of management information on the sheet-shaped device;

FIG. 8 is a table illustrating periodically aggregated data of detection data, held in a database, of the sensor group of the sheet-shaped device;

DETAILED DESCRIPTION

Figure 1:
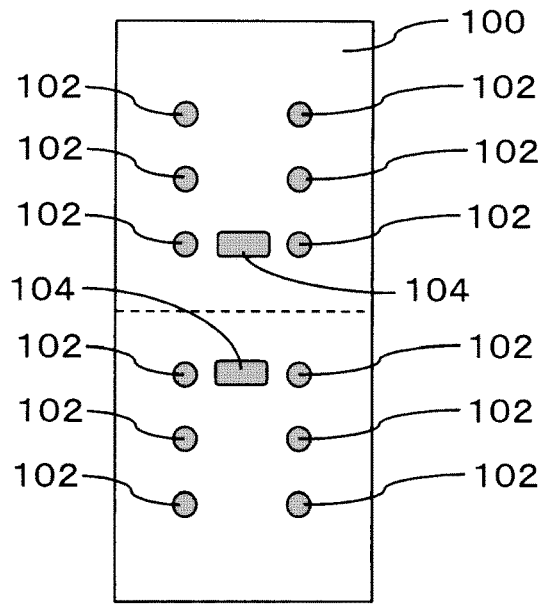
FIG. 1 is a view illustrating an example of sensor arrangement in a sheet-shaped device.
Figure 2:
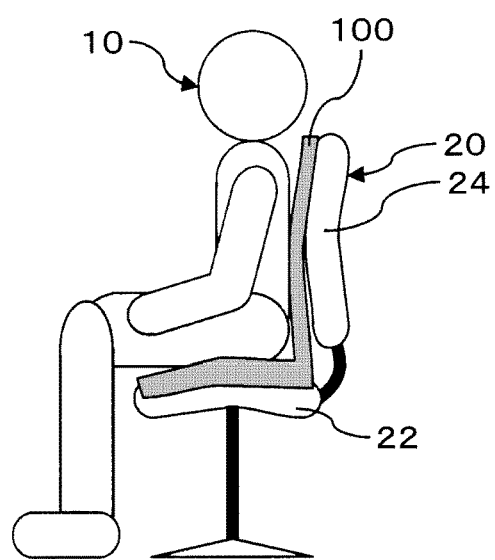
FIG. 2 is a view schematically illustrating a use state of the sheet-shaped device.

A sheet-shaped device 100 of the exemplary embodiment will be described with reference to FIGS. 1 and 2. As illustrated in FIGS. 1 and 2, the sheet-shaped device 100 is a rectangular relatively thin device that has, for instance, a width of an approximately human shoulder width and a length of approximately the length from the neck to the root of the thigh of a human. The "relatively thin" herein indicates that the sheet-shaped device 100 is thin enough to be portable with wounded or folded. The sheet-shaped device 100 is used by overlaying it on a range from a seat 22 to a backrest 24 of a chair 20, for instance. It is to be noted that FIG. 2 illustrates the sheet-shaped device 100 with a thickness larger than actual dimensions to make the sheet-shaped device 100 more visible. Also, the sheet-shaped device 100 is used by covering a body part of a user with it, like a lap robe for keeping the legs of a seated user warm.

As illustrated in FIG. 1, in the sheet-shaped device 100, a group of load sensors 102 and a group of temperature sensors 104 are disposed symmetrically with respect to the center (which is illustrated by a dashed line in FIG. 1, however, a mark indicating the center of the sheet-shaped device 100 does not have to be provided) of the sheet-shaped device 100 in a longitudinal direction.

The group of load sensors 102 is distributed over a wide range of the seat surface of the seat 22 of the chair 20 so that the sitting (seated) posture of a user can be evaluated. For instance, the group of load sensors 102 is disposed at a position below the buttocks or the thighs of both legs of a user when the sheet-shaped device 100 is properly placed on the chair 20 (for instance, the central portion illustrated by a dashed line is installed by positioning to the boundary between the seat 22 and the backrest 24 of the chair 20), and the user takes a proper sitting posture. The reason why the group of load sensors 102 is distributed by being divided on the right and left is to make it possible to determine on which side (the right or the left) the weight of a user is applied when sitting. Also, the reason why the load sensors 102 are provided at different positions in a lengthwise direction is to make it possible to determine, for instance, how deep a user is sitting back. The arrangement of the load sensors 102 in two rows as illustrated in FIG. 1 is merely an example. Alternatively, instead of the group of load sensors 102, a sheet-shaped pressure distribution sensor capable of measuring a pressure distribution on a surface may be provided. In this case, the pressure distribution sensor may be built in the sheet-shaped device 100, for instance, in a size and an installation range which covers at least the range (the range excluding the portions of the sheet-shaped device 100 which hang back down from the upper surface of the backrest 24 or hang down from the front end of the seat 22 when the sheet-shaped device 100 is overlaid on a standard chair), which corresponds to the seat surface, of the sheet-shaped device 100.

One purpose for providing the group of temperature sensors 104 is to detect that a user is using the sheet-shaped device 100 as a lap robe. When a user sits on the sheet-shaped device 100 placed on the chair 20, whether or not a user is sitting can be determined from detection information of the group of load sensors 102. On the other hand, when a user seated on the chair 20 is using the sheet-shaped device 100 as a lap robe, detected load of the group of load sensors 102 is hardly different from detected load when the sheet-shaped device 100 not in use is placed on the chair 20 or a desk, for instance. Thus, in this example, when temperatures detected by temperature sensors 104 are within a temperature range (for instance, the range of approximately 28 to 37 degrees Celsius) determined based on human body temperature, it is determined that the sheet-shaped device 100 is "used" as a lap robe or as a seat cushion placed on a chair. For this purpose, when the sheet-shaped device 100 is used as a lap robe, the temperature sensors 104 are disposed at a location near the body (for instance, the thighs) of a user. When the sheet-shaped device 100 is used as a lap robe, a position in the vicinity of the central portion of the sheet-shaped device 100 in the longitudinal direction is likely to be in contact with the thighs of a user, thus the temperature sensors 104 may be disposed at such a position. Alternatively, the number of temperature sensors 104 to be provided may be increased to enhance the possibility of contact between one of the temperature sensors 104 and positions at which the body temperature of a user is detectable.

In the arrangement formation of the sensor group illustrated in FIG. 1, the load sensors 102 are symmetrically arranged so that any side of the sheet-shaped device 100 in the longitudinal direction may be disposed on the upper side (that is, the backrest side). However, this is merely an example. When portions, which are overlaid on the backrest 24 of the chair 20 and the seat 22, of the sheet-shaped device 100 are separated, and the sheet-shaped device 100 can be properly installed in the chair 20 by a user in accordance with the separation, the arrangement of the load sensors 102 may be made different between the seat 22 and the backrest 24.

In addition to the arrangement illustrated in FIG. 1, the sheet-shaped device 100 may include a humidity sensor, a position sensor that detects the position of the sheet-shaped device 100 by utilizing a publicly known positioning system such as an indoor positioning system using the Global positioning System (GPS) and/or radio waves, and a sensor (hereinafter referred to as a "sensor sheet") using an optical fiber array in a sheet arrangement similarly to the fiber array disclosed in United States Unexamined Patent Application Publication No. 2017/0215736. When a sensor of the optical fiber array is used, the sensor is provided at least in the portion, placed on the seat 22 of the chair 20, of the sheet-shaped device 100.

The sheet-shaped device 100 may be configurated by these sensors, the later-described controller 110, communicator 112 (see FIG. 3), and power supply circuit (and an internal battery as a power source depending on situations), a base sheet in which wires for connecting the later-described components are provided, and a cover that detachably covers the base sheet. The base seat is composed of a flexible material in order to be used as a lap robe. The cover may be composed of cloth which is formed by weaving or knitting, for instance, wool or chemical fiber. The cover may be designed to be removed and washable when the cover becomes dirty.

The sheet-shaped device 100 is flexible as described above, and is portable in a rolled state, for instance. The sheet-shaped device 100 adheres to the surface of the backrest 24 of the chair 20 due to, for instance, frictional force generated on the cloth of the cover (or further utilizing weight balance achieved by hanging part of the sheet-shaped devices 100 to the back side over the upper portion of the backrest 24), and does not slip down.

Figure 3:
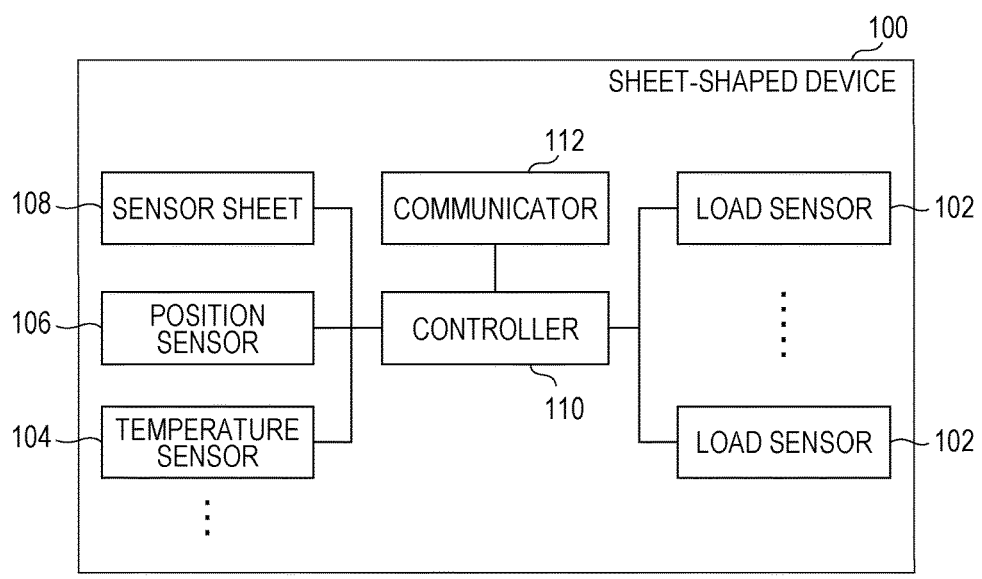
FIG. 3 is a diagram illustrating a functional configuration of the sheet-shaped device.

Next, an example of electrical functional configuration of the sheet-shaped device 100 will be described with reference to FIG. 3. In the example of FIG. 3, the sheet-shaped device 100 includes a group of load sensors 102, a group of temperature sensors 104, a position sensor 106, a sensor sheet 108, a controller 110, and a communicator 112.

The load sensor 102 is a sensor that detects a magnitude of force applied to the sensor. The load sensor 102 may be a pressure sensor. Each temperature sensor 104 is a sensor that detects temperature, and may be a sensor that has a sufficient sensitivity in a range from a room temperature (for instance, ten and several degrees) to approximately human body temperature. The position sensor 106 is a sensor that measures the current position (that is, the current position of the sheet-shaped device 100) of the position sensor 106 utilizing a positioning system such as GPS. Also, instead of providing the sheet-shaped device 100 with the position sensor 106, position information detected by a position sensor (such as GPS sensor) of a mobile terminal 200 communicating with the sheet-shaped device 100 by a proximity communication system may be used as the position information on the sheet-shaped device 100.

The sensor sheet 108 includes a sheet, a light source, a light detector, a signal processing circuit, and a control circuit of an optical fiber array that operates on the same principle as the optical fiber array disclosed in United States Unexamined Patent Application Publication No. 2017/0215736. The control circuit controls the light source, and performs control to supply a predetermined input optical signal to the sheet of the optical fiber array. Also, the signal processing circuit converts the input optical signal from the sheet of the optical fiber array into an electrical signal, and performs processing to extract a pulse rate and the other target information by performing the analysis disclosed in United States Unexamined Patent Application Publication No. 2017/0215736. The sheet-shaped device 100 may include a sensor other than the sensors illustrated. For instance, the sheet-shaped device 100 may have an acceleration sensor and/or an illuminance sensor.

The controller 110 receives detection signals and detection data (hereinafter collectively referred to as detection data) from these sensors, and processes the detection data. The processing performed by the controller 110 may include, for instance, processing to transmit a group of the detection data to a server 250 (see FIG. 4) via the communicator 112. Also, the controller 110 may analyze the detection data obtained from the sensor group, and may calculate an analysis result. For instance, the controller 110 may determine as to the quality (good or bad) and the type of the sitting posture of a user from a combination of detected loads of the group of load sensors 102. Instead of the detection data obtained from the sensor group or along with the detection data, the controller 110 may transmit information on analysis results obtained by analyzing the detection data to the server 250 directly or via the mobile terminal 200. The analysis of the detection data of the sensor group may be performed by a sheet cooperative application 204 in the mobile terminal 200 of a user or by the server 250. Alternatively, the controller 110, the sheet cooperative application 204, and the server 250 may share the analysis for the detection data group. Also, when devices that actively operate, such as a lamp and a loudspeaker are built in the sheet-shaped device 100, the controller 110 may control the operation of those devices according to the detection data from the sensors and instructions from the mobile terminal 200.

The communicator 112 is a device for performing data communication in conformity with one of communication standards. In one example, the communicator 112 communicates with the mobile terminal 200 (a smartphone, or a tablet terminal) held by a user in accordance with a predetermined proximity communication standard. The proximity communication standard used here is, for instance, a wireless communication standard with a target of a personal area (for instance, a range of several tens cm to several m), such as Bluetooth (registered trademark), Zigbee (trademark), and Z-Wave (trademark). In this example, the communicator 112 transmits information from the sensors to the mobile terminal 200 (see FIG. 4), the information being obtained by the above-described sensor group under the control of the controller 110. In this case, the information detected by the sensors is transmitted to the server 250 via the mobile terminal 200. Also, in another example, the communicator 112 may use the mobile phone standard or a standard allowing wide area communication, such as various communication standards (for instance, LoRa and SIGFOX) classified as Low Power Wide Area (LPWA), and may transmit the information detected by the sensor group to the server 250 in a "direct" manner without passing through the mobile terminal 200. The "direct" transmission referred to herein includes transmission via a relay device in conformity with the above-mentioned standard.

Each component in the sheet-shaped device 100 operates by receiving power supply from an external power source such as a commercial power source and/or a built-in battery (for instance, a rechargeable battery) of the component.

Figure 4:
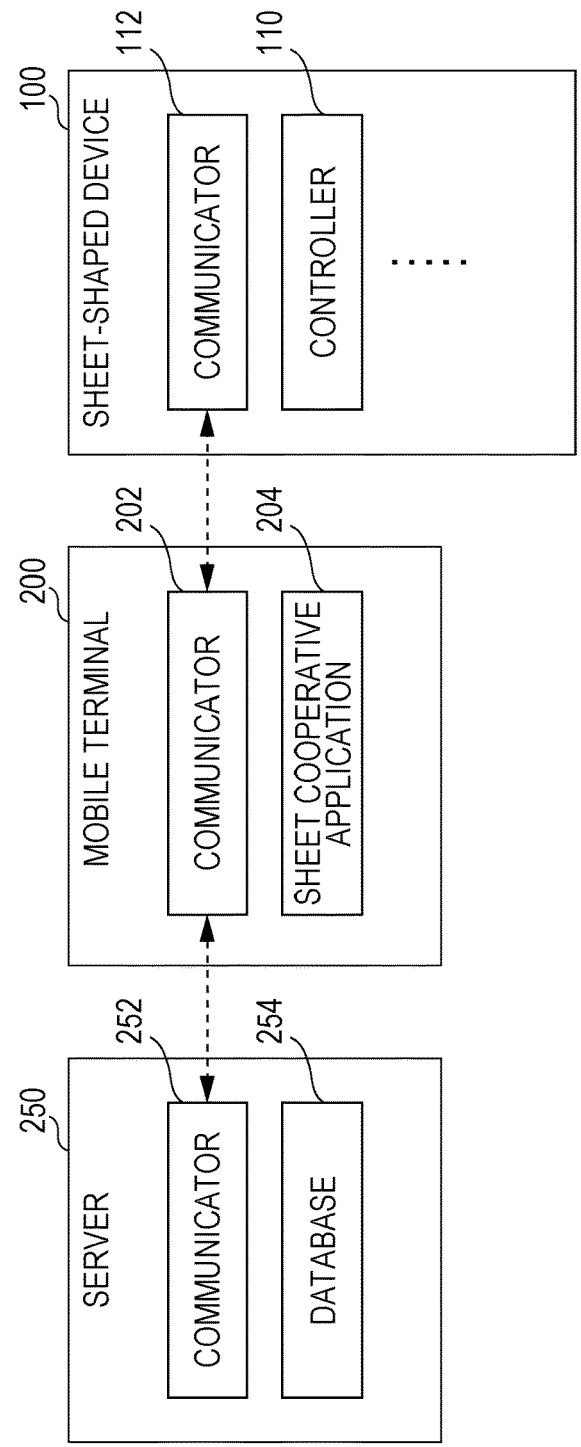
FIG. 4 is a diagram illustrating a functional configuration of a system including the sheet-shaped device, a mobile terminal, and a server.

Next, an example of a system configuration of the exemplary embodiment will be described with reference to FIG. 4. The mobile terminal 200 used and carried by a user sitting on the chair 20 in which the sheet-shaped device 100 is installed can communicate with the communicator 112.

The mobile terminal 200 includes the communicator 202, and in the illustrated example, can communicate with the communicator 112 of the sheet-shaped device 100, for instance, by a proximity communication system by the communicator 202. Also, the sheet cooperative application 204 is installed in the mobile terminal 200. The sheet cooperative application 204 is application software that provides information processing service related to the sheet-shaped device 100 to a user using information received from the communicator 112 of the sheet-shaped device 100 or information obtained from the server 250. The sheet cooperative application 204 displays a screen on which information detected by the sensor group of the sheet-shaped device 100 and useful information for a user, obtained by analyzing secondary information (for instance the weather when the information is detected) derived from the detected information are displayed. The information displayed by the sheet cooperative application 204 is, for instance, information for health and cosmetic care of a user (for instance, a working woman). For instance, the length of a time during which a user is seated, and the posture of a user when seated are analyzed, and provides a screen for warning a user about an adverse effect on health and cosmetic care due to continuous sitting for a long time or a bad sitting posture, and information on results of analysis of daily activities of a user from a viewpoint of sitting (a detailed example will be described later). Also, the sheet cooperative application 204 may analyze a detection data group received from the sheet-shaped device 100. The sheet cooperative application 204 may transmit the detection data group received from the sheet-shaped device 100, results of analysis of the data group, or both detection data group and results of analysis to the server 250 via the communicator 202.

In the illustrated example, the server 250 includes a communicator 252, and receives from the communicator 202 of the mobile terminal 200, for instance, the detection data and results of analysis received by the mobile terminal 200 from the sheet-shaped device 100. The received data is registered in a database 254 in association with a user ID (identification information) which is associated with the sheet-shaped device 100. Also, the server 250 may analyze the received data, and register results of the analysis in the database 254 in association with the user ID. Also, the server 250 may generate information to be provided to users using the data stored in the database 254. The provided information generated by the server 250 may be in the form of Web page, for instance.

One of the features of the sheet-shaped device 100 of the exemplary embodiment is that use in an underlay mode and use in a cover mode are both assumed. The underlay mode is a mode in which the sheet-shaped device 100 is placed on the seat of the chair 20, and a user sits on the sheet-shaped device 100. The cover mode is a mode in which a user sitting on a seat covers the knees or another part of the body with the sheet-shaped device 100 for protection against cold. In the exemplary embodiment, it is determined from detection data of the sensor group included in the sheet-shaped device 100 whether the use mode of the sheet-shaped device 100 is the underlay mode or the cover mode. A result of the determination is accumulated in the database 254, and utilized for analysis of the detection data of another sensor group and provision of information to users.

Figure 5:
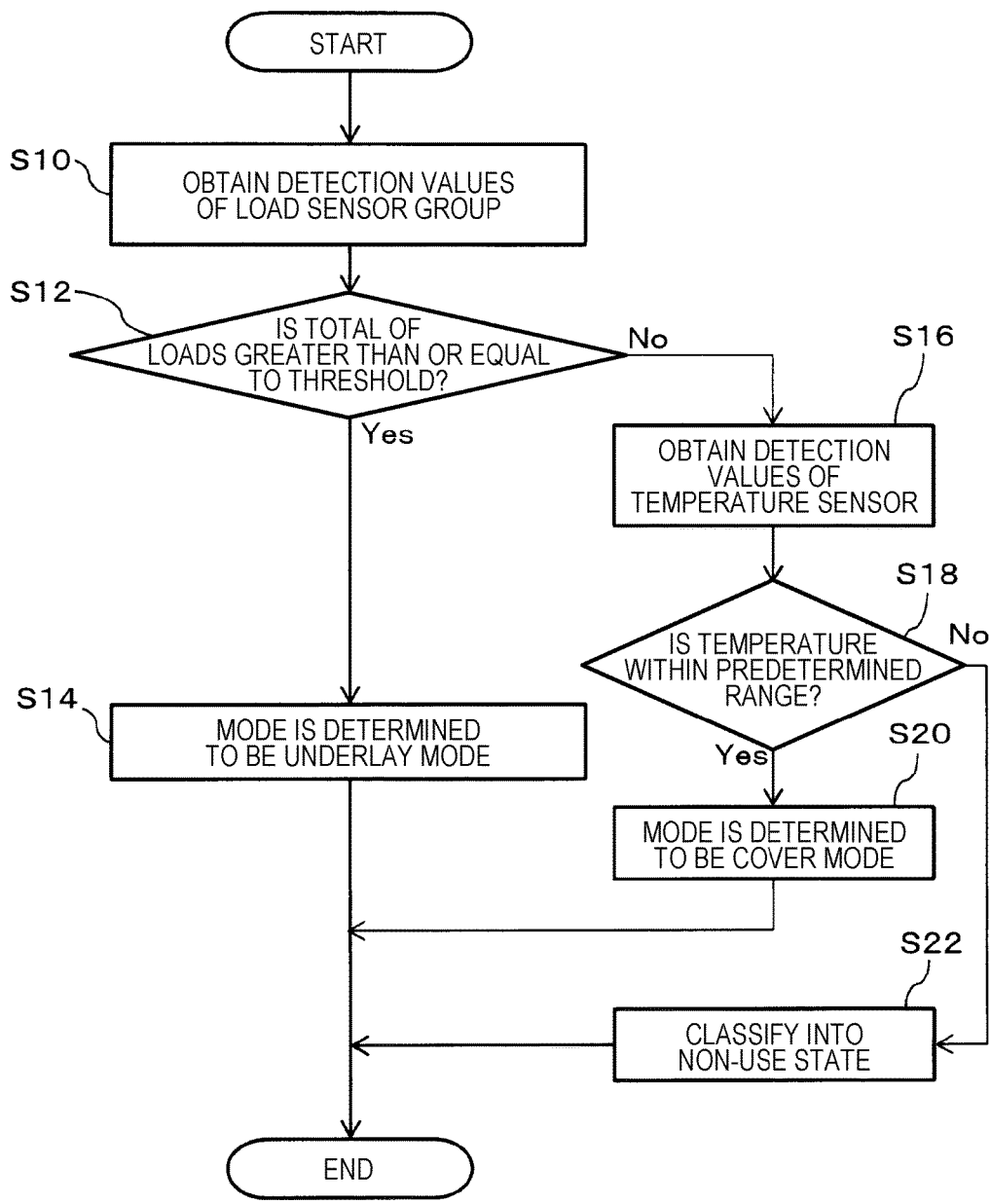
FIG. 5 is a flowchart illustrating the steps to determine a use mode of the sheet-shaped device.

An example of steps for determining a mode is illustrated in FIG. 5. The processing steps illustrated in FIG. 5 may be performed by the controller 110 in the sheet-shaped device 100, or the sheet cooperative application 204 in the mobile terminal 200 or the server 250 which has received the detection data of the sensor group in the sheet-shaped device 100. Hereinafter a description is given under the assumption that the controller 110 performs an operation as an example.

In the processing, the controller 110 first obtains detection values of the group of load sensors 102 (S10), and determines whether or not the sum of those detection values is greater than or equal to a predetermined threshold (S12). When a determination result in S12 is Yes, the controller 110 determines that the sheet-shaped device 100 is used in the underlay mode (S14). This is because when a user sits on the sheet-shaped device 100 underlaid, the weight of the user is applied to the group of load sensors 102. The threshold used for determination in S12 is defined based on the weight of the user or a standard human weight. The threshold is set to the value of several ten percent of the weight because when a user is sitting, the entire weight of the user is not necessarily applied to the seat.

When the determination result in S12 is No, there is nothing placed or an object very lighter than a human (for instance, a bag or a small article) is placed on the sheet-shaped device 100. This case includes both situations: one in which a user is using the sheet-shaped device 100 in the cover mode, the other in which a user leaves the sheet-shaped device 100 on a seat or a desk (in other words, the sheet-shaped device 100 is not in use). The controller 110 determines whether the sheet-shaped device 100 is in use in the cover mode based on detection data of the temperature sensors 104. Specifically, the controller 110 obtains detection values of the temperature sensors 104 (S16), and determines whether at least one of those detection values is in a predetermined temperature range determined based on human body temperature (S18). The temperature range used for determination in S18 is set to a range slightly lower than the human body temperature because the temperature sensors 104 are in contact with the body of a user with clothes between the temperature sensors 104 and the body of the user. When the determination result in S18 is Yes, the controller 110 determines that the sheet-shaped device 100 is used in the cover mode (S20). When the determination result in S18 is No, the controller 110 determines that the sheet-shaped device 100 is in a non-use state (S22). The non-use state is a state in which a user does not use the sheet-shaped device 100 in the underlay mode and the cover mode. In one example, a non-use state is considered to be a state in which a user is not seated.

In the examples above, determination between the underlay mode and the non-use state is performed based on the detection temperatures of the temperature sensors 104. However, this is merely an example. In addition to this, for instance, detection signals of the sensor sheet 108 are obtained in S16, and it is determined in S18 whether or not the detection signals include a signal indicating pulse or breathing. When a result of the determination is Yes, it may be determined that the sheet-shaped device 100 is used in the cover mode, and when a result of the determination is No, it may be determined that the sheet-shaped device 100 is in the non-use state. Also, the sheet-shaped device 100 may be provided with an acceleration sensor, and it is determined in S18 whether or not a state in which an acceleration detected by the acceleration sensor is a predetermined threshold near 0 or lower has continued for a predetermined time or longer. When a result of the determination is No, the current mode may be determined to be the cover mode, and when a result of the determination is Yes, the current state may be determined to be the non-use state.

The temperature sensors 104, the sensor sheet 108, and the acceleration sensor are each sensor that detects movement or phenomenon caused by the organic activity (for instance, a temperature due to a body temperature, periodic fine movement of the body due to heart rate or pulse, and an acceleration due to movement of the body) of a user who uses the sheet-shaped device 100 in the underlay mode or the cover mode. In addition to the temperature sensors 104, the sensor sheet 108, and the acceleration sensor, a sensor which detects movement or phenomenon caused by the organic activity of a user may be provided in the sheet-shaped device 100. Even when the group of load sensors 102 has not detected a load which is considered to be the weight of a user, if the sensor has detected movement or phenomenon caused by the organic activity of the user, the controller 110 determines that the sheet-shaped device 100 is used in the cover mode by the user.

Also, determination may be made between the cover mode and the non-use state by combining multiple sensors. For instance, when at least one the conditions below is met in S18, the current mode may be determined to be cover mode, and when the both conditions are met, the current state may be determined to be the non-use state: a first condition that one of detection values of the temperature sensors 104 is within a predetermined range for determining a human body temperature, and a second condition that the duration of a state in which a detection value of the acceleration sensor is a predetermined threshold near 0 or lower is shorter than a predetermined time. Also, depending on the manner in which conditions for detection values of the sensor group are set, any of the condition for determining the underlay mode, the condition for determining the cover mode, and the condition for determining the non-use state may not be met. When it is not possible to determine any mode or any state like this, the current mode or state may be classified as a fourth state which is "unknown", for instance. Although the detection data classified as unknown is recorded on the database 254, the detection data is not used for analysis for the case where a user is seated.

The controller 110 performs the steps for determining a mode described above on a regular basis, for instance.

Also, immediately after a user leaves a seat and changes its state from a state (that is, the underlay mode) in which the user is sitting on the sheet-shaped device 100 on a seat, almost no load is applied to the group of load sensors 102, and the current state is such that the group of temperature sensors 104 has detected a temperature near the body temperature of the user. In the steps of FIG. 5, the state is be determined to be the cover mode, and to avoid this situation, for instance, immediately after the current state changes from a state which is determined to be the underlay mode to a state in which the condition for determining the underlay mode is not met by the detection values of the group of load sensors 102, the current mode is not immediately determined to the cover mode, but may be determined to a special state such as "unknown" or "underlay mode completed". When it is certain that the detected temperature of the temperature sensor 104 does not meet the condition in S18 after waiting for a predetermined cooling period (for instance, approximately several minutes), the state in the past at the time point when the underlay mode was completed may be determined to be the "non-use state". When determination is made between the non-use state, the cover mode, and the underlay mode by comprehensively analyzing the detection data of multiple sensors including the sensor sheet 108 and the acceleration sensor, it is also possible to determine that the current state is the non-use state immediately after a user stands up from the sheet-shaped device 100.

The controller 110 of the sheet-shaped device 100 obtains detection data of the sensors (such as the group of load sensors 102, the temperature sensor 104) in the sheet-shaped device 100, for instance, on a regular basis (every second merely as an example), and transmits the detection data to the server 250. Also, instead of the detection data group of the sensor group or in addition to the detection data group, the controller 110 may transmit analysis results (for instance, a result of determination of a sitting posture) obtained by analyzing the detection data group to the server 250 on a regular basis, for instance. The transmission may be through the mobile terminal 200 of a user, which is connected via proximity communication or may be direct transmission using the protocol for LPWA. When the transmission is via the mobile terminal 200, the sheet cooperative application 204 of the mobile terminal 200 transmits a pair of detection values and analysis results received from the controller 110 to the server 250 in association with a user ID (this is held in the sheet cooperative application 204) that identifies the user account on the server. Also, in the case where transmission is directly performed from the sheet-shaped device 100 to the server 250, the controller 110 transmits detection values and analysis results of the sensors to the server 250 in association with a user ID or a device ID of the sheet-shaped device 100. The user ID may be set in the controller 110, for instance, from the sheet cooperative application 204 of the mobile terminal 200 of a user. Also, once a correspondence relationship between the device ID of the sheet-shaped device 100 and the user ID is registered in the server 250, when the controller 110 transmits information such as a detection value to the server 250 in association with a device ID, the server 250 can determine the user ID for the information.

When receiving detection data and analysis results of the sensor group of the sheet-shaped device 100, the server 250 registers the received data along with information at the date/time of the reception in the database 254 as record data for a user ID corresponding to the received data.

In the above, the controller 110 collectively transmits a set of detection data and analysis results of all the sensors in the sheet-shaped device 100 the server 250 on a regular basis. However, this is merely an example. Instead, for instance, detection is performed at different timings and time intervals for each sensor or each sensor group of the same type, and detection data and analysis results obtained as a result may be transmitted to the server 250.

Instead of transmission on a regular basis, only when large change occurs in the server 250, the detection data and analysis results may be transmitted to the server 250. An example of large change is change in the use mode (the underlay, the cover, and the non-use state) of the sheet-shaped device 100. Also, change in the classification (for instance, classification between a good posture and a bad posture, or more particularly, classification between posture types such as a normal posture, a hunched posture and a leaning back posture) of sitting posture of a user is also an example of large change which acts as a trigger of notification to the server 250. Also, when the position detected by the position sensor 106 is changed (for instance, when a user moves to another room), or when the heart rate or the breathing rate of a user reaches a dangerous level, large change is considered to occur, and the detection data then may be transmitted to the server 250. When it is determined from the detection data of the sensor group that predetermined large change has occurred, the controller 110 itself or the sheet cooperative application 204 which receives and analyzes the detection data from the controller 110 transmits the detection data of the sensor group then, a set of analysis results of the detection data, or only the detection data or analysis results related to large change to the server 250.

Next, an example of data registered in the database 254 of the server 250 will be described.

FIG. 6 illustrates an example of data originated from the sensor group of a sheet-shaped device 100 corresponding to a user ID "user-A" in the database 254 of the server 250. As illustrated, in association with the date/time of reception of data from the controller 110 or the sheet cooperative application 204, information items received then are registered in the database 254 for individual users. These information items includes, for instance, the use mode (the underlay mode, the cover mode, and the non-use state) of the sheet-shaped device 100, the position detected by the position sensor 106, a set of detection loads of the group of load sensors 102, a classification (classification between a good posture and a bad posture in the illustrated example) of sitting posture determined from the set of detection loads, and a heart rate determined from the sensor sheet 108. Regarding the information item "position" among these items, a pair the latitude and the longitude detected by the position sensor 106 (when the position sensor 106 is compliant with GPS) may be recorded as it is, the name (such as a building name, an office name, or a room name) at a location corresponding to the pair, obtained from a map data base (not illustrated) may be recorded, or both the pair and the name may be recorded. Since a sitting posture is determined from the detection values of the group of load sensors 102, the sitting posture is unknown in a mode other than the underlay mode. In the illustrated example, the heart rate is recorded only in the underlay mode. However, when a reliable heart rate is obtained from the sensor sheet 108 even in the cover mode, a heart rate may be recorded in the cover mode, too. Also, in the case of the cover mode and the non-use state, loads detected by the load sensors 102 have no meaning, thus, a set of detection loads are not recorded. However, in the case of the "unknown" state not corresponding to none of the underlay mode, the cover mode, and the non-use state, a set of detection loads may be recorded on the database 254 in preparation for the later analysis (the same goes with other detection data such as a heart rate).

FIG. 6 illustrates an example in which only when a "large change" occurs, data is transmitted from the controller 110 to the server 250. When data is transmitted from the controller 110 to the server 250 on a regular basis, the data transmitted on a regular basis along with the date/time of reception of the data are recorded on the database 254.

The information item group illustrated in FIG. 6 is merely an example. In addition to these, other information items originated from the detection data of the sensor group in the sheet-shaped device 100 may be recorded on the database 254. Alternatively, some of the information items recorded on the database 254 may be determined by the server 250 analyzing the data received from the controller 110.

Also, in addition to the information items (which are called primary information) illustrated in FIG. 6 directly originated from the detection data of the sensor group of the sheet-shaped device 100, the database 254 may record second information which can be obtained from other databases and sensors on the network using the primary information as a key. For instance, when the server 250 receives primary information from the controller 110, from a sensor (for instance, a room temperature sensor or a humidity sensor in a room) at a location indicated by position information included in the primary information, information on the detection data (for instance, the temperature and the humidity of a room) of the sensor may be obtained, and the information on the detection data may be recorded on the database 254 as the secondary information then in association with the primary information. From a combination of date/time and a position included in the primary information, the weather at the date/time in a region corresponding to the position may be obtained from a weather information service on the Internet, and may be recorded on the database 254. The information in a server on the Internet can be retrieved later as necessary, thus when the primary information is obtained, the primary information does not need to be recorded on the database 254 by the server 250.

Also, management information for individual users may be held in the database 254. FIG. 7 illustrates an example of such user management information. The illustrated user management information includes a user ID, a sheet device ID, a dirt coefficient in the underlay mode, a dirt coefficient in the cover mode, and a cumulative dirt value for each of users. As the sheet-shaped device 100 is repeatedly used, the cover becomes dirty, and a dirt coefficient indicates conditions of dirt according to frequency of use. In the illustrated example, how much stain is accumulated on the cover per hour in each of the underlay and cover modes is expressed numerically as a dirt coefficient. In the illustrated example, the value of a dirt coefficient is determined based on the upper limit (100 in the illustrated example) of the cumulative dirt value, and the upper limit is a value for the state in which the cover is very dirty. For instance, a user himself/herself logs in the server 250 and sets the dirt coefficient in each mode. The cumulative dirt value is the sum of products of a dirt coefficient in each mode and a corresponding continuation time, and indicates a degree of dirt of the current cover (28 relative to the upper limit 100 in the illustrated example). When a user cleans the cover and notifies the server 250 of the cleaning, the cumulative dirt value is reset to 0. Information on dirt coefficient and cumulative dirt value is utilized for screen display provided to users by the server 250 (the details will be described later).

Also, the server 250 may aggregate the record data illustrated in FIG. 6, and may register the aggregate results in the database 254. FIG. 8 illustrates an example of such data registered in the database 254. This example indicates data obtained by aggregating a time seated, a good posture time, and a bad posture time daily from the record data of a user "user-A". For instance, the server 250 registers in the database 254 the sum of time intervals in which the use mode corresponds to the underlay mode or the cover mode in a day, as the time seated in the day. When the current mode is the underlay mode or the cover mode, a user can be considered to be sitting on a seat, thus the total time in both modes gives the time seated. Since the record data illustrated in FIG. 6 is recorded when a large change, such as a change in the use mode, occurs, the time since the underlay mode is recorded until the next another mode is recorded is determined to be a time in which the underlay mode continues. In the example of FIG. 6, first, the underlay mode continues for 45 minutes from 9:15 to 9:50, and the underlay mode also continues for 2 hours and 8 minutes from 9:54 to 12:02. Similarly, the time since the cover mode is recorded until the next another mode is recorded is counted as the continuation time of the cover mode.

An underlay time and a cover time are each the sum of the times in which the underlay mode and the cover mode are recorded, respectively in one day in the record data of FIG. 6.

Also, the good posture time and the bad posture time are each the total value of the times in which the posture is determined to be "good" and "bad" in one day in the record data of FIG. 6. The time interval from a time when the posture is "good" in the record data to a time when the subsequent posture has a value other than "good" is the continuation time of good posture. The total of the continuation time in one day is calculated as the good posture time of the day, and is recorded on the database 254. The same goes with the bad posture time.

Although an example of daily aggregated data is illustrated in FIG. 8, aggregated data in another period such as weekly or monthly may be calculated and recorded. Such aggregated data does not need to be generated in advance, and in response to a request from a user, the server 250 may dynamically aggregate raw record data (FIG. 6).

Next, an example of a screen provided to users by the server 250 will be described.

Figure 9:
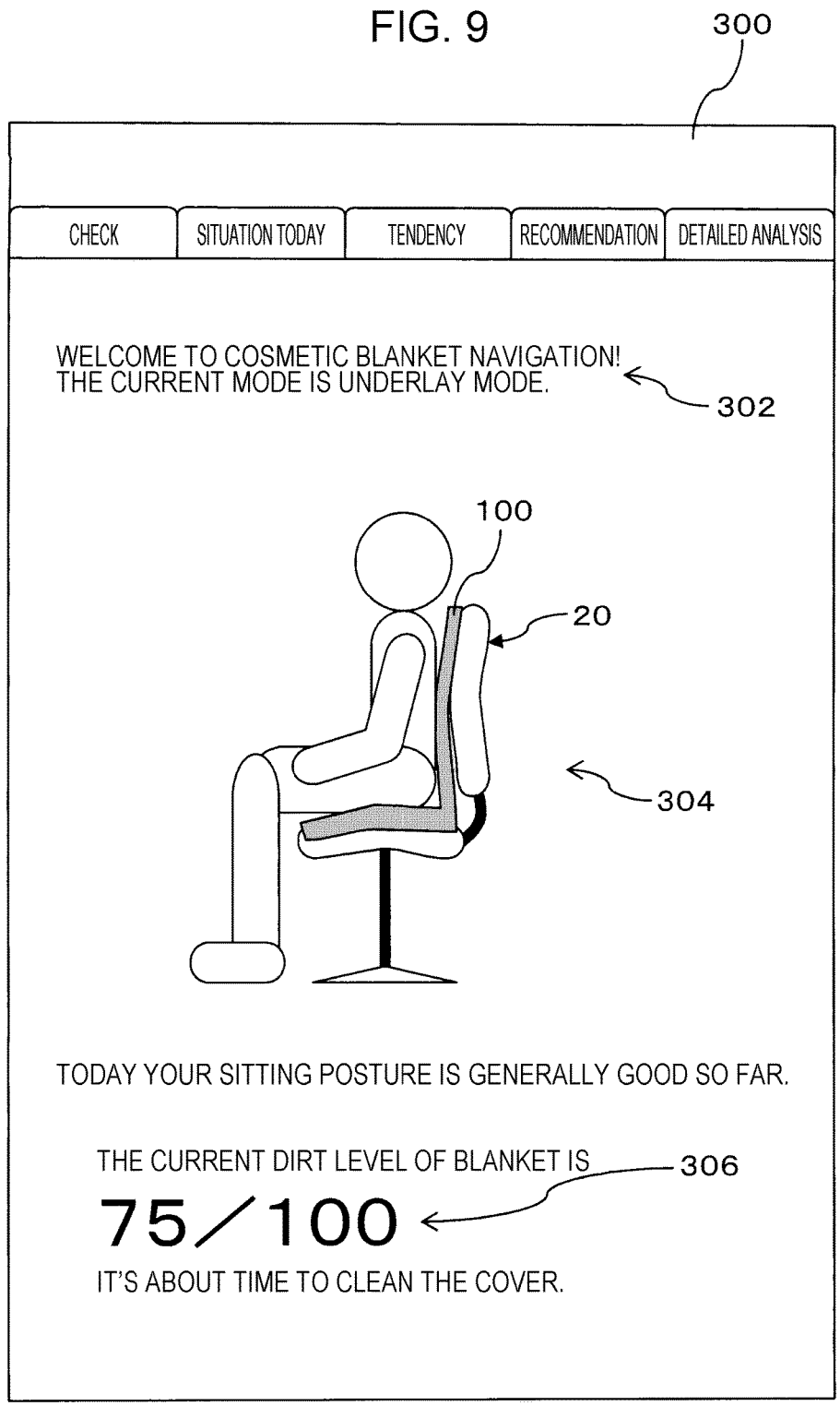
FIG. 9 is a view schematically illustrating a display example of a home screen provided by a sheet cooperative application.
Figure 10:
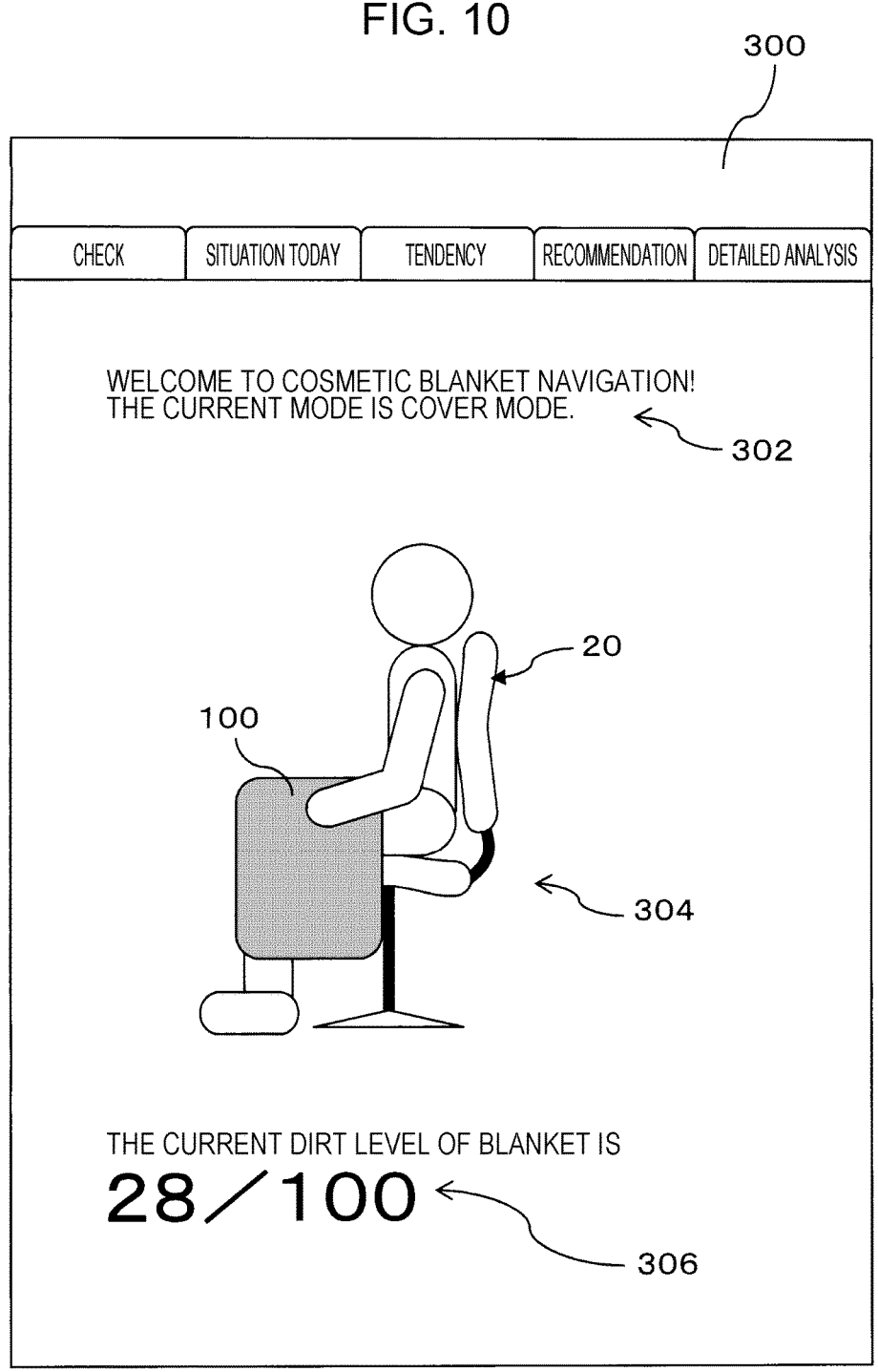
FIG. 10 is a view schematically illustrating a display example of the home screen provided by the sheet cooperative application.

FIGS. 9 and 10 are each a view schematically illustrating display of a home screen 300 provided by the sheet cooperative application 204. The illustrated home screen 300 contains a current use mode 302 of the sheet-shaped device 100, an image display 304 of the use mode, and display of a dirt level 306 of the sheet-shaped device 100. The image display 304 schematically illustrates a user sitting on the chair 20, and a state of the sheet-shaped device 100 according to the use mode. FIG. 9 illustrates a screen in the underlay mode, and indicates a state in which the sheet-shaped device 100 is installed under a user. FIG. 10 illustrates a screen in the cover mode, and indicates a state in which the knees of a sitting user are covered with the sheet-shaped device 100. Also, the dirt level 306 is a cumulative dirt value (see FIG. 7) which is managed in the database 254 in association with the ID of the user. The value of the dirt level 306 is reflected to the display color of the sheet-shaped device 100 in the image display 304. A higher dirt level 306 indicates more blackish color display color of the sheet-shaped device 100. In the user interface (UI) of the sheet cooperative application 204, the sheet-shaped device 100 is called by the name of "blanket".

The server 250 generates such home screen 300, for instance, in the form of Web page, and provides the home screen 300 to the sheet cooperative application 204 of a user who has logged in the server 250. The server 250 also generates various screens described below using the record data of the user in the database 254 and information available from other servers or databases on the network, and provides the various screens to the mobile terminal 200 or the personal computer of the user.

Although an example has been illustrated above in which a dirt level of the sheet-shaped device 100 is displayed, not only dirt, but wear and another degree of deterioration of the sheet-shaped device 100 and the cover as part of the sheet-shaped device 100 may be expressed numerically by the same method as in the case of dirt level, and information may be provided to users.

Figure 11:
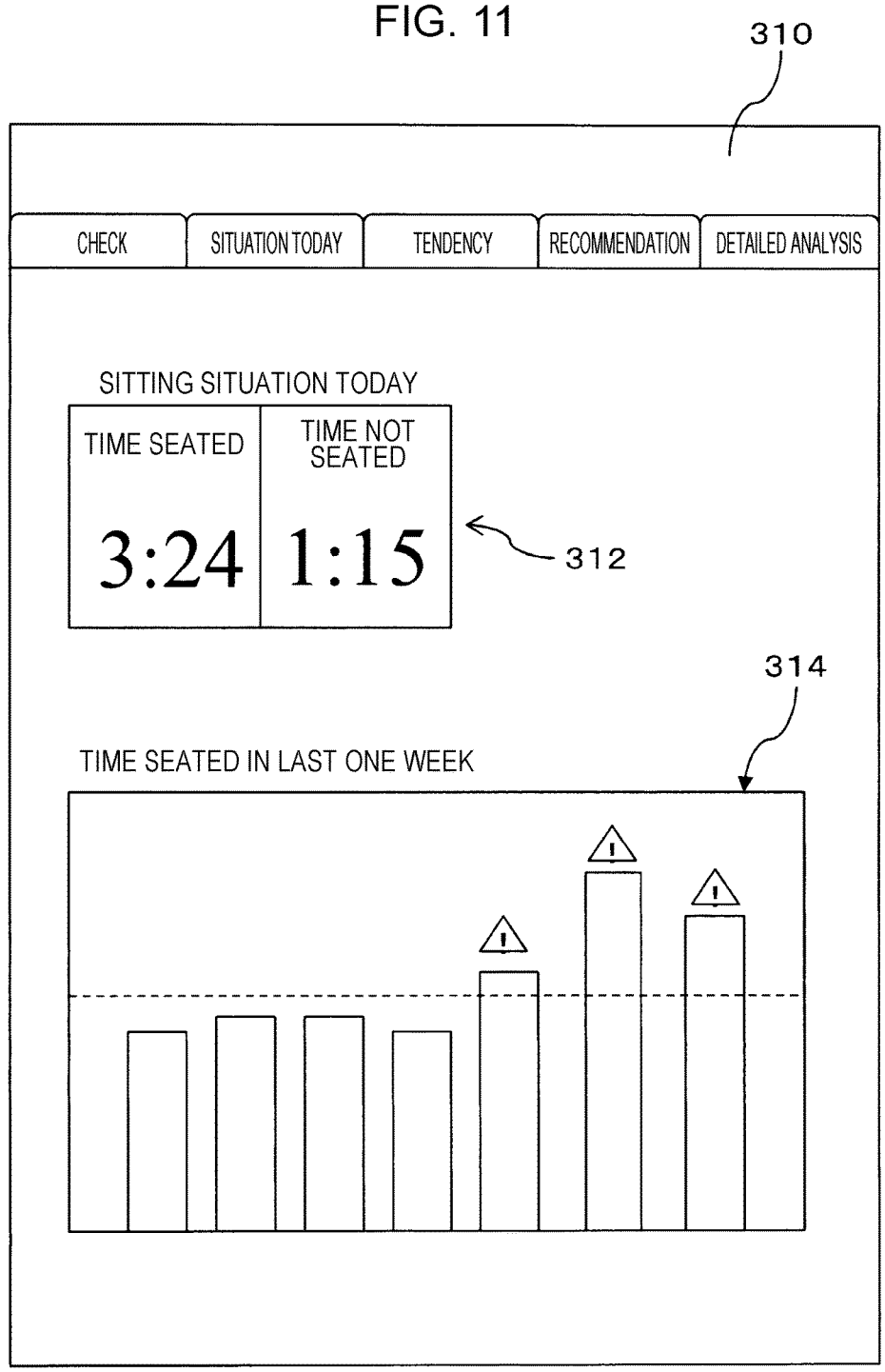
FIG. 11 is a view schematically illustrating an example of another screen provided by the sheet cooperative application.

FIG. 11 illustrates a "situation today" screen 310 which is provided to a user by the server 250. On the screen 310, primary information obtained today from the sensor group of the sheet-shaped device 100, and a summary of secondary information related to the primary information are displayed. In the illustrated example, on the screen 310, a seating situation today 312, and transition of time seated 314 in the last week are displayed. The seating situation today 312 displays the time seated of a user, and the time in a state other than seated (for instance, a state in which a user is away from a seat) during the time period from the beginning (for instance, go-to-office time of a user) of today to a time when the screen 310 is displayed. The time seated is the sum of time intervals corresponding to the underlay mode or the cover mode until the time point of today. Also, the time in a state other than seated is the remaining time obtained by excluding the time seated from the time period from the beginning of today until the current time point. Also, the time seated 314 in the last week illustrates the time seated on each day during a week until today or yesterday by a bar graph. In this display, for a bar graph for a day with a long time seated exceeding a predetermined threshold (illustrated by a dashed line in FIG. 11), a mark calling attention (a mark in which an exclamation mark is included in a triangle on top of a bar graph) displayed. In addition, on the screen 310, the weather, the temperature, the humidity of today, the current position (for instance, a room in which a user is now), the room temperature, and the humidity of a user, temporal transition of the use mode of today, and recommended information from the server 250 may be displayed. The recommended information is a message selected by an internal rule of the server 250 according to, for instance, the use mode and the time seated in today, and transition of the time seated 314 in the last week. For instance, when the time seated exceeds a threshold in many days, a message for recommendation of standing up and taking physical action is displayed as the recommended information.

In addition, on the screen 310 or another screen, the current environmental information (for instance, a pair of the room temperature and the humidity) of the current position (detected by the position sensor of the sheet-shaped device 100 or the mobile terminal 200) of a user, and an explanation from the viewpoint of cosmetic care related to the environmental information may be displayed. The current environmental information of the current position of a user may be obtained from a sensor in the vicinity of the current position by the server 250 via the Internet. Also, the explanation from the viewpoint of cosmetic care is an explanatory note indicating an evaluation such that the humidity is too low, slightly low, or appropriate from the viewpoint of cosmetic care, or similar evaluation for the room temperature. Also, the server 250 may obtain environmental information for each of the whereabouts (such as an office) of a user in the past, recorded in the record data in the database 254, and may create a ranking of the degree of recommendation for those positions (such as an office) from the viewpoint of cosmetic care. The server 250 may provide a user with a screen that displays which level the current position of a user is in the ranking.

Figure 12:
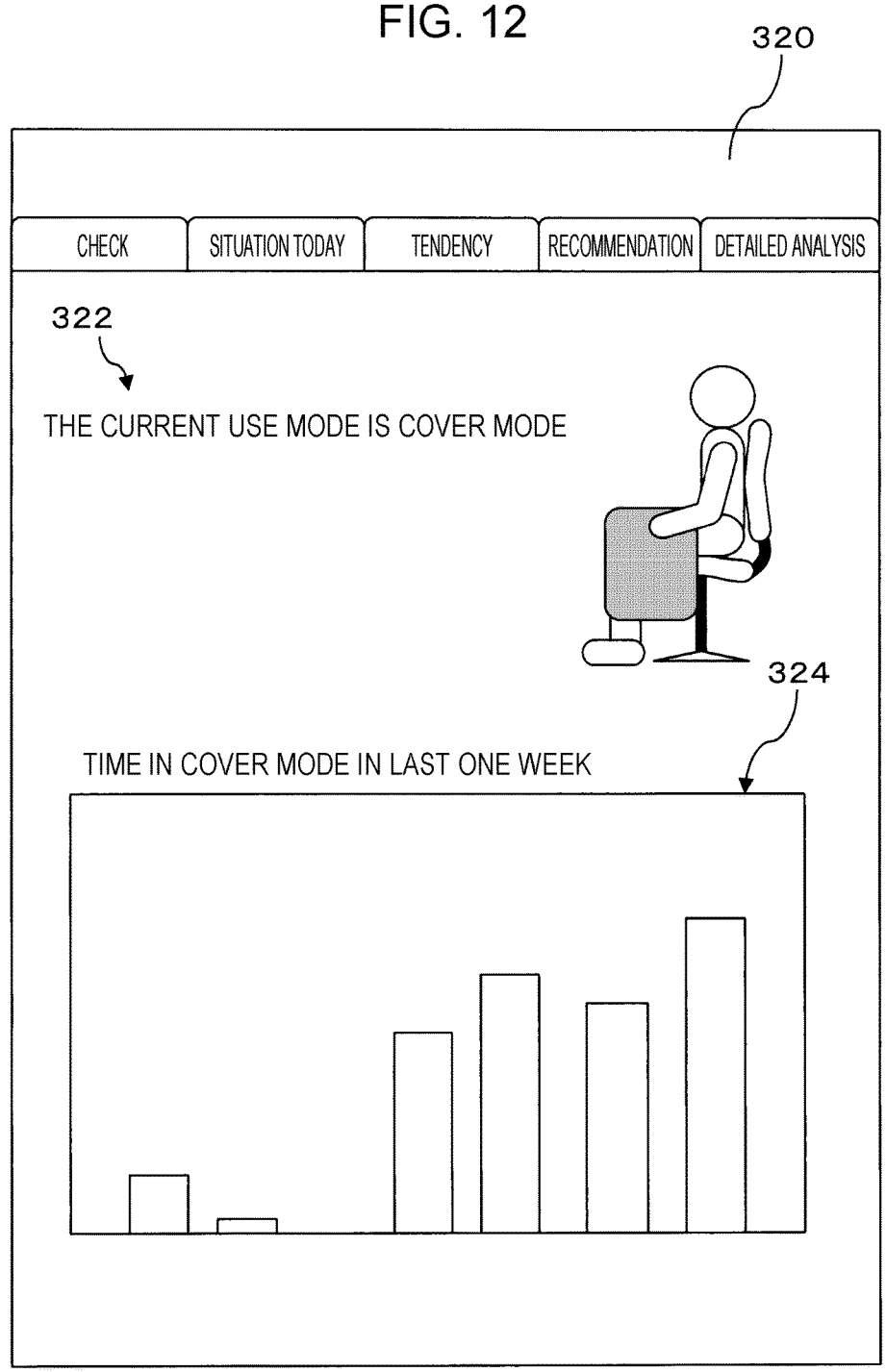
FIG. 12 is a view schematically illustrating an example of another screen provided by the sheet cooperative application.

FIG. 12 illustrates a current mode screen 320. The current mode screen 320 is a screen that provides information related to the current use mode of the sheet-shaped device 100. In the illustrated example, on the current mode screen 320, a current use mode 322, and temporal transition information 324 on the mode in the last week are displayed. In the temporal transition information 324, the total value of the operating time of the sheet-shaped device 100 in the current use mode in each day of the last week is illustrated by a bar graph.

On the current mode screen 320, not only the temporal transition information 324, but also results of aggregation and analysis of relevant information of the user in the past (for instance, the position, the posture, the heart rate, the room temperature, and the weather at that time) when the use mode was the same as the current use mode may be displayed. For instance, positions (for instance, an office or a room) at which the current use mode is used for a long time may be displayed in a ranking format, or a ratio of the current use mode at the current position to the other use mode may be displayed as an example.

Figure 13:
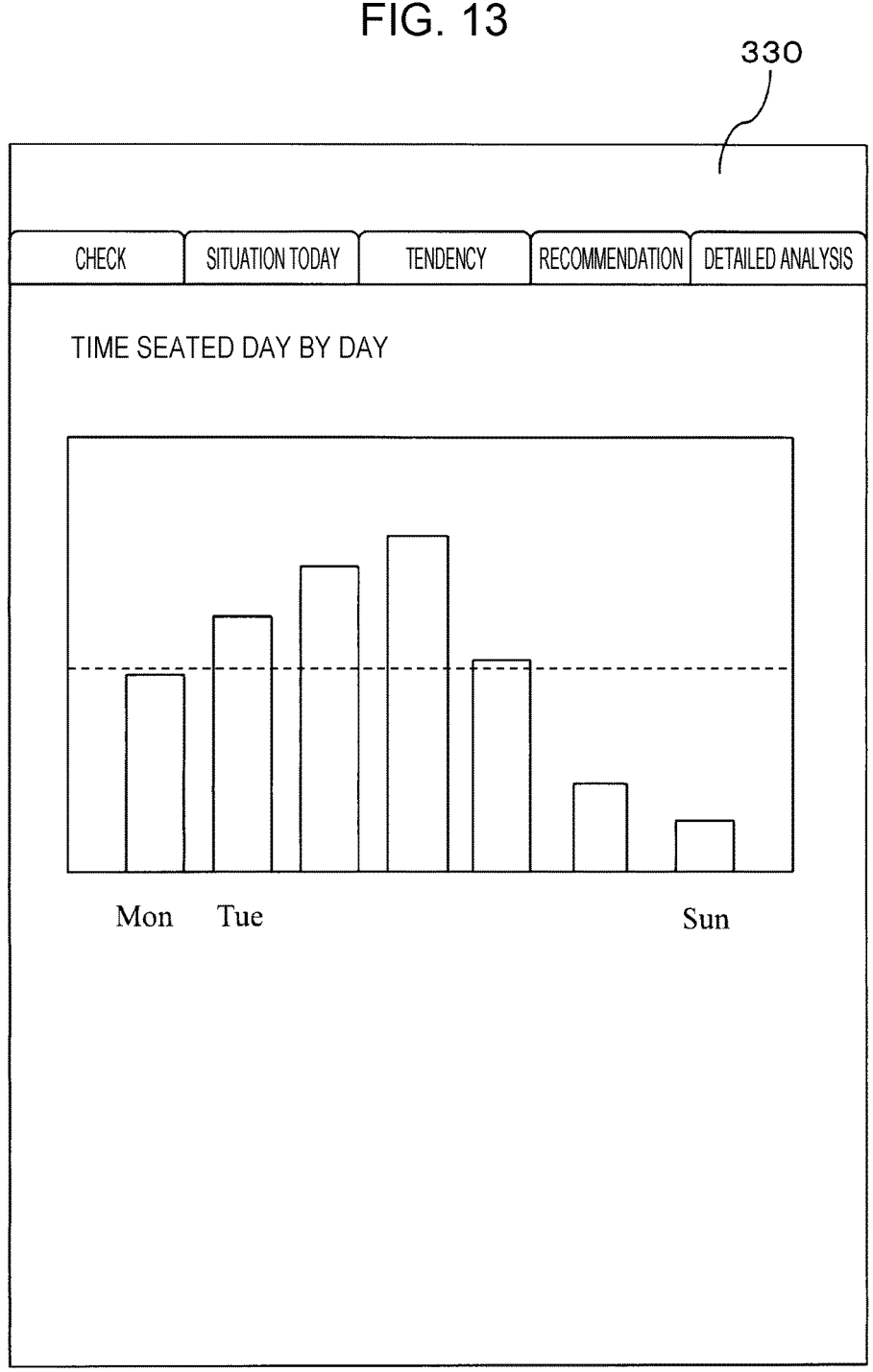
FIG. 13 is a view schematically illustrating an example of another screen provided by the sheet cooperative application.

Also, the server 250 aggregates or analyzes the record data of a user and secondary information related to the record data from various viewpoints, and provides a user with a screen that displays results of the aggregation or analysis. FIG. 13 illustrates a display example of "time seated day by day" screen 330 which is one of the screens mentioned above. On the screen 330, the average value of time seated of the user in the past is illustrated day by day using a bar graph. Similarly, the average time of each of the underlay mode and the cover mode may be displayed day by day. On the screen 330, a comment for results of analysis of the tendency of the time seated day by day, and/or a text explaining an improvement proposal to the tendency may be displayed.

Although the example of FIG. 13 provides daily aggregation, the server 250 may provide results of aggregation and analysis based on other viewpoints, such as aggregation and analysis according to other positions (for instance, an office, a room, or a cafe), time zones (such as in the morning, in the afternoon, and overtime hours), terms (for instance, every month, in every quarter), the weather, and temperature zones of room temperature. Also, the server 250 may provide results of aggregation and analysis based on a combination of multiple viewpoints. For instance, the average of time seated according to a combination of position and day may be provided as an example. In addition to the time seated and the time in each use mode, aggregation and analysis of such various viewpoints or a combination of viewpoints may be applied to various data such as a continuation time (for instance, a cumulative total per day), and a heart rate in each sitting posture.

Also, the server 250 provides various information using information on the "position" of the record data. For instance, the server 250 aggregates the room temperature and the humidity (specifically, the temperature and the humidity detected at the date/time by a temperature sensor and a humidity sensor installed in an office or a room corresponding to the position) for each office or room, corresponding to a combination of the date/time and the position of each record included in the record data (see FIG. 6) of a user in the database 254, and calculates an average temperature and an average humidity for each office or room, for instance. When an office or a room having a room temperature and a humidity in a range of recommended room temperature and humidity for cosmetics purpose is registered in the server 250, the server 250 provides a user with a screen that displays such an office or a room as a recommended office. The screen displays information such as the name of recommended office, a map of the surrounding areas, a time zone when the office is available, the environmental information (for instance, average room temperature and humidity) on the office, and the distance from the current position of a user (the mobile terminal 200).

Also, the server 250 may determine a ratio of use modes for each position (such as an office or a room) from the data in the database 254, and may provide information based on the ratio. For instance, the ratio of use modes for each position is information indicating a ratio of times, specifically the operating time of the sheet-shaped device 100 in the underlay mode is such percentage and the operating time of the sheet-shaped device 100 in the cover mode is such percentage (in other words, the proportion of the time in each of the underlay mode and the cover mode out of the time seated). The server 250 may provide a user with a screen that displays the ratio information on the current position (the mobile terminal 200) of a user.

When a user feels cold in the lower body, it is probable that the sheet-shaped device 100 is used in the cover mode. Thus, as a location where a user feels cold in the lower body, the server 250 may provide a user with a screen that introduces an office or a room in which the ratio of the cover mode in the past is higher than or equal to a predetermined threshold. Conversely, as a location where a user doesn't feel cold in the lower body, the server 250 may provide a user with a screen that introduces an office with a low ratio of the cover mode.

Also, the server 250 or the sheet cooperative application 204 may provide a user with a check screen for the sitting posture. When a user calls the check screen via the mobile terminal 200, the server 250 or the sheet cooperative application 204 receives detection data of the load sensors 102 from the controller 110 of the sheet-shaped device 100, and determines whether the current sitting posture of the user is good or bad based on the detection data. A screen which indicates a result of the determination is displayed on the mobile terminal 200.

Also, when the sitting posture of a user detected by the sheet-shaped device 100 satisfies various alarm conditions, the sheet cooperative application 204 or the server 250 may display an alarm screen according to the alarm conditions. Various conditions may be considered as the alarm conditions, for instance, a first condition that a bad sitting posture has continued for a threshold time or longer, a second condition that the time seated has continued for another threshold time or longer, and a third condition that days, on which the time seated exceeds still another threshold time, have continued for a threshold number of days or longer. For instance, when the first condition is satisfied, the sheet-shaped device 100 displays on the mobile terminal 200 a notification indicating that the posture is not proper and/or an alarm screen which displays advice for returning to the proper posture. For instance, the sheet cooperative application 204 or the server 250 sends a push notification associated with the alarm screen to the mobile terminal 200, a user who has noticed the push notification calls the screen. For each of other conditions such as the second condition, and the third condition, an alarm screen is prepared which is to be displayed when the condition is satisfied. For instance, for the second condition, an alarm screen is prepared which displays a message indicating that a user is sitting for a long time and/or a message for prompting a user to do stretching exercise. For the third condition, an alarm screen is prepared which displays and recommends some exercises for relaxation.

Also, the sheet-shaped device 100 may be utilized to measure the weight of a user daily, and a result of the measurement may be recorded on the server 250 and analyzed. In the case of a normal sitting posture, the legs touch the floor, and the elbows are placed on the armrest, thus the entire weight of a user is not applied to the group of load sensors 102. Thus, a weight measurement mode is set in the sheet cooperative application 204. When a user selects the mode, the sheet cooperative application 204 displays a screen that explains a posture for weight measurement (for instance, the posture in which both legs are off the floor, no weight is applied to the backrest, and the elbows are not placed on the armrest) using images or a text. For instance, a countdown screen for starting weight measurement is displayed, and when measurement is started, a screen indicating that the posture to be maintained for a predetermined time (for instance, several seconds) is displayed. For instance, the time average of the loads detected by the group of load sensors 102 during the measurement period is the result of measurement of the weight of a user. After the measurement is completed, the sheet cooperative application 204 displays a screen that presents the value of measured weight. On the screen, a graph indicating transition of the weight in the last several days may be displayed as well. Also, when the measured weight exceeds the upper limit or falls below the lower limit of a predetermined desirable weight range determined based on the height of a user, the sheet cooperative application 204 may display an alarm screen. Alternatively, a user may register an ideal weight of the user in the sheet cooperative application 204 or the server 250, and when the difference between the measured weight and the ideal weight exceeds a threshold, an alarm screen may be displayed.

Also, the server 250 may analyze the correlation between the items of primary information obtained from the sheet-shaped device 100, and the items of secondary information related to the items of primary information, and may provide a user with results of the analysis. For instance, the server 250 may generate a graph indicating monthly transition of the time seated (the average value per day in the month) and the weight (the average in the month), and may provide the sheet cooperative application 204 with the graph. Also, the server 250 may determine a correlation between the temperature and the weight, and may provide the sheet cooperative application 204 with a screen that displays the contents of the correlation. Also, the server 250 may analyze the correlation between the place (such as an office) of a user identified from the position information and the time seated at the place, and may display results of the analysis.

In the exemplary embodiment described above, an example has been illustrated in which a database, which accumulates primary information originated from the sensor group of the sheet-shaped device 100 and secondary information related to the primary information, is included in the server 250 on the network. However, this is merely an example. A system configuration may be adopted in which the database 254 is included in the mobile terminal 200, and the sheet cooperative application 204 in the mobile terminal 200 performs analysis and control similarly to the server 250.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing system comprising:
   a sheet that is usable in a use mode which is any one of an underlay mode and a cover mode;
   an accumulation unit that accumulates relevant information related to when the sheet is used in association with the use mode of the sheet when being used; and
   a presentation unit that presents a result of analysis of the information accumulated in the accumulation unit, in consideration of the use mode.

2. The information processing system according to claim 1, further comprising
   a unit that determines a current use mode of the sheet,
   wherein of a group of pieces of information accumulated in the accumulation unit, the presentation unit presents a result of analysis based on a piece of information corresponding to the determined current use mode.

3. The information processing system according to claim 1,
   wherein the presentation unit presents aggregate information which is aggregated by assigning a set weight to each of the relevant information accumulated in association with the underlay mode and the relevant information accumulated in association with the cover mode.

4. The information processing system according to claim 2,
   wherein the presentation unit presents aggregate information which is aggregated by assigning a set weight to each of the relevant information accumulated in association with the underlay mode and the relevant information accumulated in association with the cover mode.

5. The information processing system according to claim 3, further comprising
   a unit that, as the weight of each of the underlay mode and the cover mode, holds a value that indicates a degree of deterioration of the sheet per unit time when the sheet is used in the mode,
   wherein the presentation unit determines a value that indicates the degree of deterioration of the sheet by aggregating an operating time of the sheet in the underlay mode and an operating time of the sheet in the cover mode by assigning the weight for each the underlay mode and the cover mode to the corresponding operating time, and presents the determined value.

6. The information processing system according to claim 4, further comprising a unit that, as the weight of each of the underlay mode and the cover mode, holds a value that indicates a degree of deterioration of the sheet per unit time when the sheet is used in the mode, wherein the presentation unit determines a value that indicates the degree of deterioration of the sheet by aggregating an operating time of the sheet in the underlay mode and an operating time of the sheet in the cover mode by assigning the weight for each the underlay mode and the cover mode to the corresponding operating time, and presents the determined value.

7. The information processing system according to claim 5,
wherein when the sheet is used in the underlay mode, the presentation unit displays a first image schematically illustrating a state in which a user sitting on the sheet installed on a seat, when the sheet is used in the cover mode, the presentation unit displays a second image schematically illustrating a state in which the sheet covers a body part of the user sitting on the seat, and a display pattern of the sheet in the first image and the second image is according to the value that indicates the degree of deterioration.

8. The information processing system according to claim 6,
wherein when the sheet is used in the underlay mode, the presentation unit displays a first image schematically illustrating a state in which a user sitting on the sheet installed on a seat, when the sheet is used in the cover mode, the presentation unit displays a second image schematically illustrating a state in which the sheet covers a body part of the user sitting on the seat, and a display pattern of the sheet in the first image and the second image is according to the value that indicates the degree of deterioration.

9. The information processing system according to claim 1, further comprising
a location identifying unit that identifies a location where the sheet is used,
wherein as the relevant information, the accumulation unit accumulates information on the location where the sheet is used identified by the location identifying unit in association with the use mode of the sheet when being used, and
the presentation unit presents information indicating a relation between the location and the use mode based on the information accumulated in the accumulation unit.

10. The information processing system according to claim 9,
wherein as the information indicating a relation between the location and the use mode, the presentation unit presents information corresponding to a ratio of use of the sheet in the cover mode at the same location.

11. The information processing system according to claim 10,
wherein the presentation unit presents the location at which the ratio of use in the cover mode is higher than or equal to a threshold, as a candidate place where a user feels cold in a lower body.

12. The information processing system according to claim 1,
wherein the accumulation unit accumulates data detected by a sensor provided in the sheet as the information related to when the sheet is used.

13. The information processing system according to claim 12,
wherein the presentation unit obtains from another device on a network secondary information having a predetermined relationship with the data accumulated in the accumulation unit, and presents a result of analysis of the data and the secondary information related to the data in consideration of the use mode.

14. The information processing system according to claim 1,
wherein the accumulation unit accumulates data obtained from an external information source of the sheet when the sheet is used as the information related to when the sheet is used.

15. The information processing system according to claim 12, further comprising
a determination unit that determines the use mode of the sheet based on the data detected by the sensor provided in the sheet.

16. The information processing system according to claim 15,
wherein the sensor provided in the sheet includes one or more first type sensors that detect a load or a pressure applied to the sheet, and
when a load greater than or equal to a threshold defined based on a human weight is detected by the one or more first type sensors, the determination unit determines that the sheet is being used in the underlay mode.

17. The information processing system according to claim 16,
wherein in addition to the one or more first type sensors, the sensor provided in the sheet includes a second type sensor that detects movement or phenomenon caused by an organic activity of a user in contact with the sheet, and
when a load greater than or equal to the threshold defined based on a human weight is not detected by the one or more first type sensors and the phenomenon is detected by the second type sensor, the determination unit determines that the sheet is being used in the cover mode.

18. The information processing system according to claim 17,
wherein when a load greater than or equal to the threshold defined based on a human weight is not detected by the one or more first type sensors and the phenomenon is not detected by the second type sensor, the determination unit determines that the sheet is in a non-use state.

19. The information processing system according to claim 1,
wherein the presentation unit presents a time during which the sheet is used in the underlay mode or the cover mode as a time during which a user is seated.

20. An information processing system comprising:
a sheet that is usable in a use mode which is any one of an underlay mode and a cover mode;
a determination unit that determines that the sheet is in one of a state in which the sheet is used in the underlay mode, a state in which the sheet is used in the cover mode, and a state in which the sheet is not used, based on data detected by one or more sensors provided in the sheet; and
a unit that calculates a time during which a user is seated based on a length of time in which the sheet is determined to be used in the underlay mode or the cover mode by the determination unit.

* * * * *